(12) United States Patent
Suganuma et al.

(10) Patent No.: US 11,092,542 B2
(45) Date of Patent: Aug. 17, 2021

(54) QUALITY EVALUATION METHOD AND QUALITY EVALUATION DEVICE

(71) Applicant: Sumitomo Electric Industries, Ltd., Osaka (JP)

(72) Inventors: Hiroshi Suganuma, Yokohama (JP); Yoko Sugiyama, Yokohama (JP); Asako Motomura, Yokohama (JP)

(73) Assignee: Sumitomo Electric Industries, Ltd., Osaka (JP)

( * ) Notice: Subject to any disclaimer, the term of this patent is extended or adjusted under 35 U.S.C. 154(b) by 269 days.

(21) Appl. No.: 16/235,018

(22) Filed: Dec. 28, 2018

(65) Prior Publication Data

US 2019/0137389 A1    May 9, 2019

Related U.S. Application Data

(63) Continuation of application No. PCT/JP2017/016656, filed on Apr. 27, 2017.

(30) Foreign Application Priority Data

Jul. 8, 2016   (JP) .............................. JP2016-135943

(51) Int. Cl.
*G01N 21/359*    (2014.01)
*C12M 1/34*    (2006.01)
(Continued)

(52) U.S. Cl.
CPC ........... *G01N 21/359* (2013.01); *C12M 41/36* (2013.01); *G01N 33/4833* (2013.01); *G01J 3/2823* (2013.01)

(58) Field of Classification Search
CPC . G01N 21/359; G01N 33/4833; C12M 41/36; G01J 3/2823
See application file for complete search history.

(56) References Cited

U.S. PATENT DOCUMENTS

| 5,206,701 | A | * | 4/1993 | Taylor | ....................... G01J 3/08 |
| | | | | | 250/339.02 |
| 5,317,156 | A | * | 5/1994 | Cooper | .................. G01N 21/39 |
| | | | | | 250/339.13 |

(Continued)

FOREIGN PATENT DOCUMENTS

| JP | 2019-207239 A | 12/2019 |
| WO | 2011/163624 A1 | 12/2011 |

(Continued)

OTHER PUBLICATIONS

Ozaki Y. et al., "Near-Infrared Spectroscopy in Biological Molecules and Tissues", In: Roberts G.C.K. (eds) Encyclopedia of Biophysics, Springer (Year: 2013).*

(Continued)

*Primary Examiner* — Blake C Riddick
(74) *Attorney, Agent, or Firm* — Baker Botts L.L.P.; Michael A. Sartori (57) ABSTRACT

A quality evaluation method includes, acquiring light intensity distribution information related to a distribution of absorbance with respect to the measurement light in the cell mass by irradiating a cell mass with measurement light including near-infrared light; and evaluating a quality of the cell mass based on the information. A quality evaluation device includes a light source that irradiates a cell mass with measurement light including near-infrared light; a light receiving unit that, by receiving transmitted light or diffusely reflected light from the cell mass, acquires light intensity distribution information related to a distribution of absorbance with respect to the measurement light in the cell mass, the transmitted light or the diffusely reflected light being emitted from the cell mass by irradiating the cell mass with the measurement light; and an analyzing unit that evaluates a quality of the cell mass based on the information.

4 Claims, 5 Drawing Sheets

(51) Int. Cl.
*G01N 33/483* (2006.01)
*G01J 3/28* (2006.01)

(56) References Cited

U.S. PATENT DOCUMENTS

| | | | |
|---|---|---|---|
| 7,840,360 B1* | 11/2010 | Micheels | G01N 21/359 |
| | | | 702/25 |
| 2007/0269382 A1* | 11/2007 | Santra | A61K 49/0002 |
| | | | 424/9.323 |
| 2012/0021453 A1* | 1/2012 | Patra | G01N 15/147 |
| | | | 435/34 |
| 2012/0082362 A1* | 4/2012 | Diem | G01N 21/31 |
| | | | 382/133 |
| 2012/0122084 A1* | 5/2012 | Wagner | G01N 15/147 |
| | | | 435/6.1 |
| 2012/0142095 A1 | 6/2012 | Yano et al. | |
| 2012/0203086 A1* | 8/2012 | Rorabaugh | A61B 3/1173 |
| | | | 600/321 |
| 2013/0002847 A1* | 1/2013 | Zahniser | G06T 7/0012 |
| | | | 348/79 |
| 2014/0356881 A1* | 12/2014 | Satoh | G01N 21/65 |
| | | | 435/7.1 |
| 2015/0085098 A1 | 3/2015 | Dowaki et al. | |
| 2015/0125388 A1* | 5/2015 | Gray | C07B 59/002 |
| | | | 424/1.65 |
| 2016/0097716 A1* | 4/2016 | Gulati | A61B 5/7267 |
| | | | 250/339.01 |
| 2016/0230167 A1* | 8/2016 | Koenig | C12N 5/0696 |
| 2016/0263249 A1* | 9/2016 | Frangioni | C09B 23/086 |
| 2017/0073627 A1* | 3/2017 | Kim | C08J 5/18 |
| 2017/0138851 A1* | 5/2017 | Ashrafi | G01N 33/487 |
| 2017/0202462 A1* | 7/2017 | Motz | A61B 5/0071 |
| 2017/0254741 A1 | 9/2017 | Suganuma et al. | |
| 2019/0358632 A1* | 11/2019 | Hassell | G01N 21/359 |

FOREIGN PATENT DOCUMENTS

| | | |
|---|---|---|
| WO | 2013086516 A1 | 6/2013 |
| WO | 2013/132734 A1 | 9/2013 |
| WO | 2016080442 A1 | 5/2016 |

OTHER PUBLICATIONS

"Hihakai Hishinshuteki na Spheroid (Saibokai) Oyobi 3D Soshiki no Hinshitsu Hyoka Hoho no Kaihatsu" (non-official translation: "Development of non-destructive, non-invasive spheroid (cell mass) and quality evaluation method of 3D tissue"), Regenerative Medicine, Feb. 22, 2016 (received date), vol. 15, special extra issue, whole No. 64, p. 350, ISSN 1347-7919 [Cited in Written Opinion provided with Form PCT/IB/338 dated Jan. 17, 2019 in counterpart PCT Application No. PCT/JP2017/016656].

Form PCT/IB/338, International Preliminary Report on Patentability and Written Opinion issued in counterpart PCT Application No. PCT/JP2017/016656, dated Jan. 17, 2019, 7 pages.

* cited by examiner

QUALITY EVALUATION METHOD AND QUALITY EVALUATION DEVICE

CROSS-REFERENCE TO RELATED APPLICATION

This is a continuation application of PCT/JP2017/016656 claiming the benefit of the Japanese Patent Application No. 2016-135943 filed on Jul. 8, 2016, which is incorporated by reference herein in its entirety.

TECHNICAL FIELD

The present invention relates to an quality evaluation method and a quality evaluation device of a cell mass.

BACKGROUND ART

Various studies have been made on methods for evaluating the culture state of cells. For example, US2012/0142095A describes a method in which an evaluation is performed by acquiring time series images of a cell mass for the purpose of checking the multi-layered state of the cell mass. Further, WO2011/163624 describes a method in which an analysis is performed by acquiring spectral images of biological samples, such as cell masses, for the purpose of detecting, for example, cell abnormalities.

SUMMARY OF INVENTION

Technical Problem

An object of the present invention is to provide a quality evaluation method and a quality evaluation device, which are capable of evaluating the quality of a cell mass in a non-destructive manner.

Solution to Problem

A quality evaluation method of the present invention includes an acquisition step of, by irradiating a cell mass with measurement light including near-infrared light, acquiring light intensity distribution information including information related to a distribution of absorbance with respect to the measurement light in the cell mass, and an evaluation step of evaluating a quality of the cell mass based on the light intensity distribution information.

In the quality evaluation method of the present invention, the evaluation step may include imaging light intensity information that is included in the light intensity distribution information and that corresponds to positions in the cell mass. Further, the evaluation step may include evaluating the quality by using numerical values included in light intensity information that is included in the light intensity distribution information and that corresponds to positions in the cell mass.

Further, a quality evaluation device of the present invention includes a light source that irradiates a cell mass with measurement light including near-infrared light; a light receiving unit that, by receiving transmitted light or diffusely reflected light from the cell mass, acquires light intensity distribution information including information related to a distribution of absorbance with respect to the measurement light in the cell mass, the transmitted light or the diffusely reflected light being emitted from the cell mass by irradiating the cell mass with the measurement light; and an analyzing unit that evaluates a quality of the cell mass based on the light intensity distribution information.

Advantageous Effects of Invention

According to the quality evaluation device and the quality evaluation method of the present invention, it is possible to evaluate the quality of a cell mass in a non-destructive/non-invasive manner.

DESCRIPTION OF EMBODIMENTS

Specific examples of a quality evaluation method and a quality evaluation device according to the present invention will be described below with reference to the drawings. It is to be noted that the present invention is not limited to these examples, but is indicated by the scope of the claims, and meanings equivalent to the scope of the claims and all modifications within the scope are intended to be included.

Even if there is no abnormality in individual cells that make up a cell mass or there are no differences in the appearance of a cell mass of, for example, a layered configuration, the quality as a cell mass, such as the cell density inside the cell mass (aggregation degree) or the activity degree of the mass as a whole (the mass cannot be maintained, etc.), may differ. Therefore, there is a desire for evaluating with high accuracy and in a non-destructive manner the quality of a cell mass, such as the aggregation degree and the activity degree of the cell mass.

Figure 1:
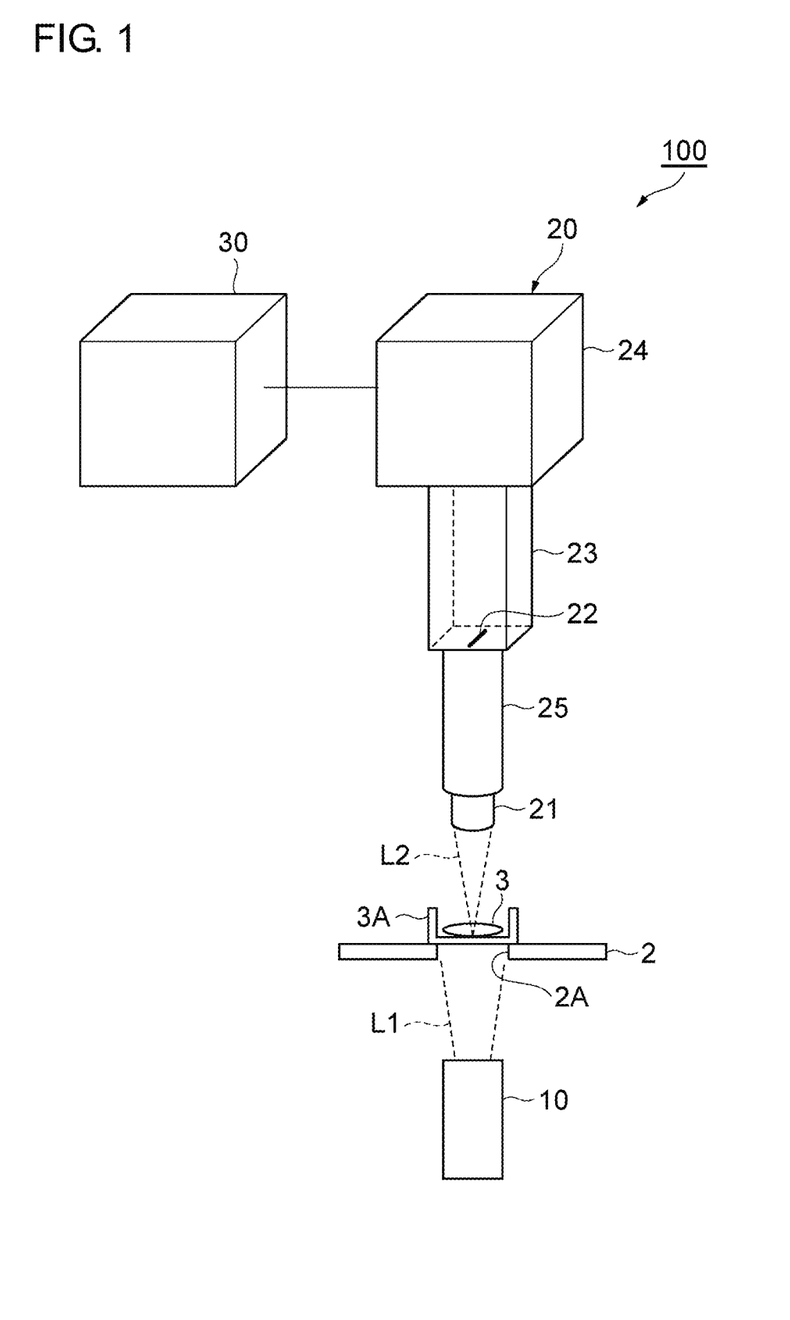
FIG. 1 is a conceptual diagram of a quality evaluation device according to an embodiment of the present invention.

FIG. 1 is a conceptual diagram of a quality evaluation device 100 according to an embodiment of the present invention. The quality evaluation device 100 is a device that evaluates the quality of a cell mass 3 placed on a moving stage 2. In this specification, the cell mass (spheroid) is a mass of aggregated cells, and includes various forms of cells, such as a two-dimensional mass and a three-dimensional mass. The cells included in the cell mass 3 are stem cells collected from animals or humans, stem cells prepared on the basis of cells collected from animals or humans, or cells differentiated from stem cells, in which cells of a plurality of cell types may be mixed in one cell mass. In addition, the "quality" of a cell mass that is evaluated by the quality evaluation device 100 refers to the "aggregation degree" of cells included in the cell mass, or the "activity degree" of cells included in the cell mass. These are indices related to an ability to maintain a life cycle, such as an ordered cell proliferation, an ability to maintain a shape as a cell mass, an ability to become a specific tissue cell, an ability to maintain a necessary function as a cell, and a tissue regeneration ability in a body of an animal or a human.

The quality evaluation device 100 receives transmitted light emitted from the cell mass 3 by irradiating the cell mass 3 with measurement light including near-infrared light to acquire light intensity distribution information including information related to the distribution of absorbance in the cell mass (acquisition step), and evaluates the quality of the cell mass 3 based on the light intensity distribution information (evaluation step). Therefore, the quality evaluation device 100 includes a light source 10, a detection unit 20, and an analyzing unit 30. The light intensity distribution information including information related to the distribution of absorbance is, for example, information related to the distribution of transmission, information related to the distribution of the intensity of transmitted light, or information related to the distribution of the intensity of diffusely reflected light.

In the embodiment below, the case where near-infrared light is used as the measurement light and information indicating the distribution of spectral data of transmitted light is used as the light intensity distribution information will be described. However, at least near-infrared light may be included as the measurement light, and light in another wavelength range may be included in the measurement light. In addition, the light intensity distribution information need not be information indicating the distribution of spectral data, and may be information indicating the distribution of absorbance with respect to light of a particular wavelength in a near-infrared region included in the measurement light. Alternatively, evaluation may be performed by acquiring spectral data of diffusely reflected light, instead of spectral data of transmitted light, and by determining the light intensity distribution information from the spectral data.

The light source 10 irradiates a predetermined area provided on the moving stage 2 with the measurement light including near-infrared light. The wavelength of the measurement light emitted by the light source 10 is appropriately selected depending on the cell mass 3. Specifically, the measurement light includes light in a wavelength range of 800 nm to 2500 nm, and, particularly, light of 1000 nm to 2300 nm. Since the near-infrared light rays in these wavelength ranges have high cell transmissivity and are influenced by vibration absorption (harmonic overtones, coupled sound) of substances, it is possible to evaluate the quality of the cell mass 3, which is a measurement object, based on these characteristics. In a case of using the measurement light of near-infrared light, it is possible to perform measurement using light in a wavelength range differing from a water absorption band; for example, light in wavelength ranges of 1000 nm to 1350 nm, and 1500 nm to 1900 nm can be used. It is to be noted that, although, in the present embodiment, the light source 10 that is formed from a halogen lamp is described, the type of the light source 10 is not particularly limited.

The light source 10 generates measurement light L1 including near-infrared light and emits it towards an opening 2A of the moving stage 2 at which the cell mass 3 is provided. It is to be noted that the light source 10 may include, for example, a waveguide optical system such as an optical fiber for irradiating the cell mass 3 with the measurement light. The measurement light L1 output from the light source 10 passes through the cell mass 3 accommodated in a container 3A on the opening 2A. Then, a part thereof is incident on the detection unit 20 as transmitted light L2.

Figure 2:
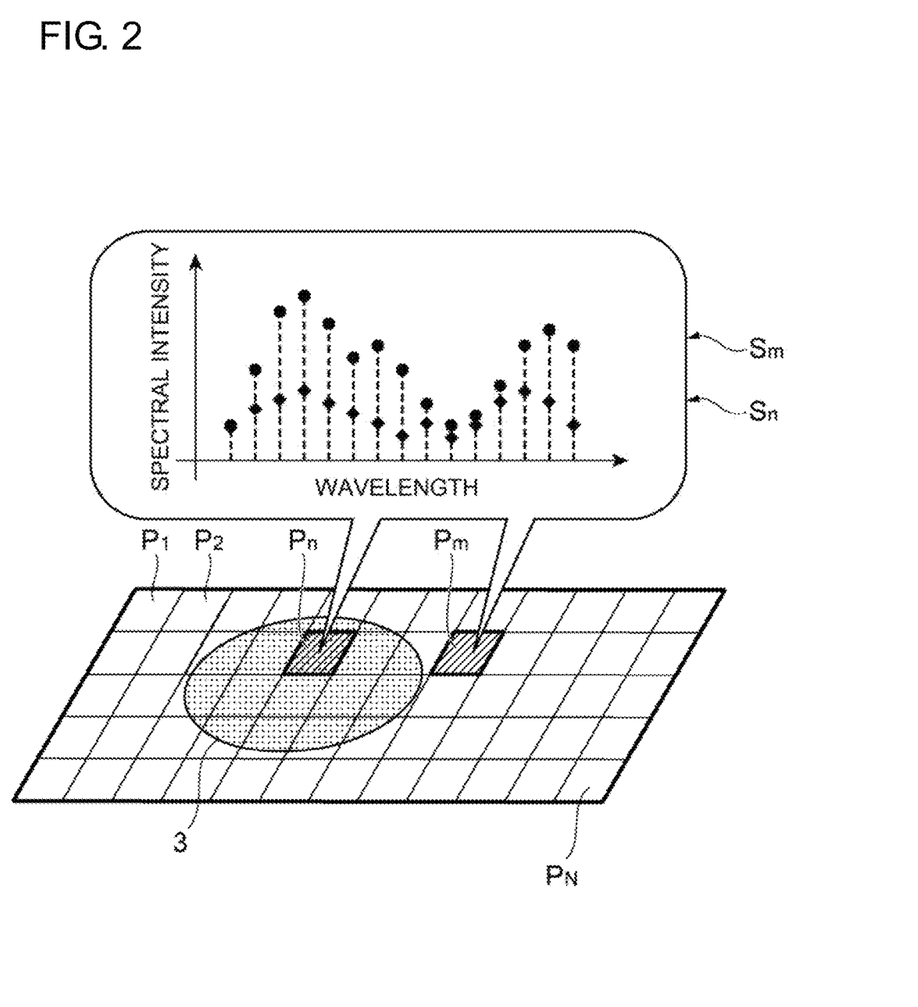
FIG. 2 is a diagram illustrating a hyperspectral image.

The detection unit 20 has a function as a hyperspectral sensor of acquiring a hyperspectral image by two-dimensionally arranged sensors. FIG. 2 is a diagram illustrating a hyperspectral image. FIG. 2 specifically shows two unit areas $P_n$ and $P_m$ of N unit areas $P_1$ to $P_N$ that make up the hyperspectral image. The unit areas $P_n$ and $P_m$ each include 15 items of intensity data at specific wavelengths (or wavelength band) as spectral information $S_n$ and spectral information $S_m$. FIG. 2 shows them in a superimposed state. In this way, based on the feature that there are a plurality of items of intensity data for each of the unit areas (pixels) constituting an image, a hyperspectral image H is data of a three-dimensional configuration having a two-dimensional element as an image and an element as spectral data. It is to be noted that, in the present embodiment, the hyperspectral image H refers to an image having intensity data in at least five wavelength bands per pixel.

FIG. 2 also shows the cell mass 3. That is, in FIG. 2, $P_n$ is a unit area (pixel) obtained by capturing the cell mass 3, and $P_m$ is a unit area (pixel) on the background (for example, the container 3A). In this way, not only the cell mass 3 but also the image obtained by capturing the background are also acquired by the detection unit 20.

Returning to FIG. 1, the detection unit 20 includes an objective lens 21, a slit 22, a spectroscopic element 23, and a light receiving unit 24. A lens barrel 25 is provided between the objective lens 21 and the slit 22.

The slit 22 extends in one direction (a direction crossing the paper surface). The transmitted light L2 that has passed through the lens barrel 25 from the objective lens 21 of the detection unit 20 and that has impinged upon the slit 22 is incident upon the spectroscopic element 23.

The spectroscopic element 23 separates the transmitted light L2 in a direction perpendicular to the longitudinal direction of the slit 22. The light separated by the spectroscopic element 23 is received by the light receiving unit 24.

The light receiving unit 24 includes a light receiving surface in which a plurality of light receiving elements are two-dimensionally arranged, and each light receiving element receives light. By this, in the light receiving unit 24, the light receiving elements arranged in a direction perpendicular to the extending direction of the slit 22 each receive light in each wavelength of the transmitted light L2 transmitted through the cell mass 3, in an area along the extending direction of the slit 22 on the moving stage 2. Each light receiving element outputs a signal corresponding to the intensity of the received light as information on one point of a two-dimensional planar shape including a position and a wavelength. The signals output from the light receiving elements of the light receiving unit 24 are sent from the detection unit 20 to the analyzing unit 30, as spectral data for each unit area (pixel) related to the hyperspectral image. In the present embodiment, the spectral data for each unit area (pixel) related to the hyperspectral image becomes the light intensity distribution information.

The analyzing unit 30 acquires the spectral data of the transmitted light L2 from the input signal, and the quality of the cell mass 3 is evaluated by using the spectral data. The evaluated results can be output from the analyzing unit 30 via an output device, such as a monitor or a printer.

The analyzing unit 30 is formed as a computer including hardware, such as a central processing unit (CPU), random access memory (RAM) and read only memory (ROM), which are main storage devices, a communication module performing communication with other devices, such as the detection unit 20, and an auxiliary storage device, such as a hard disk. The function as the analyzing unit 30 is exhibited by operating the constituent elements.

The quality evaluation device 100 can acquire a so-called one-dimensional spectral image for an area along the extending direction of the slit, by one capturing operation. Therefore, it is possible to acquire spectral data for each pixel regarding the entire cell mass 3 by moving the moving stage 2 on which the cell mass 3 is placed, or by moving a capturing area of the quality evaluation device 100.

The analyzing unit 30 acquires in advance an incident light spectrum acquired by causing the measurement light from the light source 10 to be incident upon the detection unit 20 in a state without the cell mass 3, in addition to the measurement of the spectral data related to the cell mass 3, and is able to acquire spectral data (transmitted light spectrum) related to the transmitted light which comes from the cell mass 3 from a difference between the incident light spectrum and the spectral data of the transmitted light L2 of the cell mass 3. Although the transmitted light spectrum is a spectrum related to the light transmitted through the cell mass 3, the absorbance spectrum indicating the intensity of light absorbed by the cell mass 3 can be calculated based on the incident light spectrum and the transmitted light spectrum. When the spectrum of the image obtained by capturing the background is used as the incident light spectrum, the efficiency is increased and accuracy can be realized. In the present embodiment, the absorbance spectrum is calculated and the cell mass 3 is evaluated.

It is to be noted that, as described above, image data obtained by capturing the background is also sent to the analyzing unit 30. Accordingly, first, the analyzing unit 30 extracts, of the spectral data that is sent from the detection unit 20, spectral data related to a pixel obtained by capturing the cell mass 3. Although the method of extracting spectral data related to a pixel obtained by capturing the cell mass 3 is not particularly limited, it is possible to realize a mode in which it is determined whether or not the spectral data is related to the pixel obtained by capturing the cell mass 3 based on a predetermined reference (for example, the absorbance at a particular wavelength is less than or equal to a threshold value).

The quality evaluation device 100 is configured to evaluate the quality of each mass based on information included in the absorbance spectrum of the cell mass 3. Since it can be considered that one cell mass 3 is captured with a plurality of pixels, information related to the distribution of absorbance related to light of a measurement object in the cell mass 3 is acquired by using the absorbance spectrum acquired from a plurality of pixels obtained by capturing the same cell mass 3. Then, the information is used to evaluate the quality of the cell mass 3.

As described above, the cell mass 3 is an aggregate of a plurality of cells. It can be considered that the quality of each cell mass 3 is derived from the quality of individual cells included in the cell mass 3. However, even if the quality of part of the cells included in the cell mass 3 are individually evaluated, the result and the quality of the cell mass 3 may be unrelated to each other. In addition, as described above, the quality of the cell mass 3 refers to the aggregation degree and the activity degree of the cell mass, and indicates the result of activity of each of the plurality of cells that make up the cell mass 3. Therefore, there also exist many cases in which the cells in the cell mass 3 are not uniform. Accordingly, it can be considered that, when the quality of each cell mass 3 is to be evaluated, evaluating deviations in the cell mass 3 is also effective. In the quality evaluation device 100, a relation of the absorbance distribution in the cell mass 3 and the quality of the cell mass 3 is focused and the light intensity distribution information is used as information indicating the deviations in the cell mass 3.

The light intensity distribution information includes a plurality of items of information related to the absorbance for each position in the cell mass 3. The information related to the absorbance for each position in the cell mass 3 is a set of information related to the positions in the cell mass 3 and information related to the absorbance correlated with the information indicating the positions. Although, as the information included in the light intensity distribution information and related to the absorbance for each position, an absorbance spectrum acquired for each pixel can be used, an absorbance spectrum determined from a plurality of absorbance spectra corresponding to a plurality of pixels that are adjacent to each other may be used. For example, a spectrum in which the absorbance spectra corresponding to the plurality of pixels that are adjacent to each other are averaged may be used as information related to the absorbances in areas corresponding to the plurality of pixels that are adjacent to each other. In this way, instead of the absorbance spectrum for each pixel, the absorbance spectrum determined from the absorbance spectra for the plurality of pixels may be used as the information related to the absorbance for each position in the cell mass 3.

Figure 3:
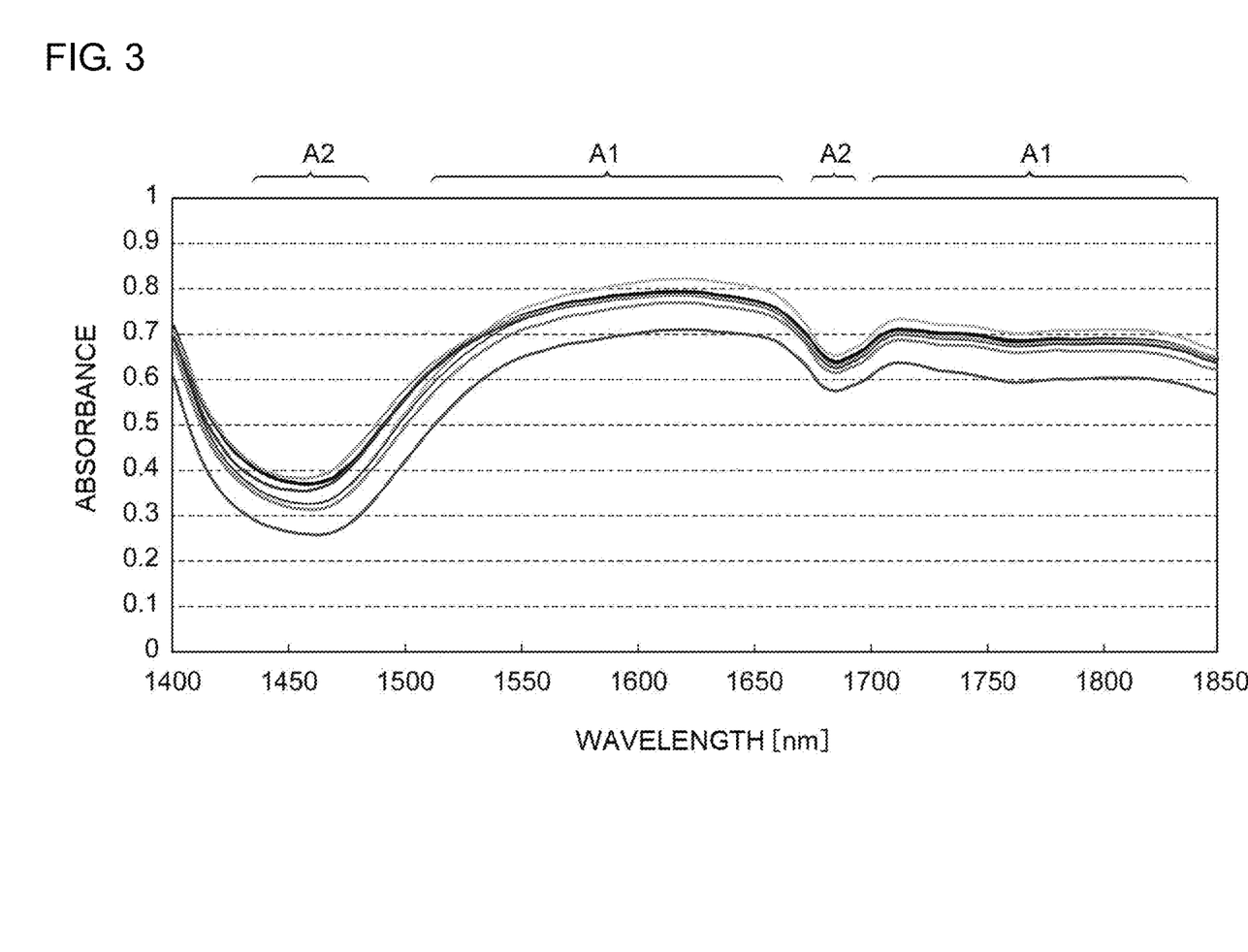
FIG. 3 is a graph of absorbance spectra acquired by irradiating cell masses with near-infrared light.

FIG. 3 is a graph of absorbance spectra acquired when a plurality of cell masses 3 related to mesenchymal stem cells have been irradiated with near-infrared light. Each of a plurality of spectra is a spectrum from substantially the same portion of the plurality of cell masses having the same culture time. The absorbance spectrum acquired from a cell mass 3 is known to change in accordance with the culture time of the cell mass 3. This is a change in accordance with the arrangement (shape) of a cell group included in the cell mass 3, or a metabolite or an internal substance of the cells that are increased or that mature due to culture. Therefore, in the present embodiment, the quality of each cell mass is evaluated by using information included in the absorbance spectrum and related to the absorbance with respect to wavelengths.

The absorbance spectra acquired from the cell masses 3 each include an wavelength area A1, where an absorption peak (high absorbance peak) exists, and an wavelength area A2, where an absorption peak (high absorbance peak) does not exist. According to the findings of the inventor, changes (intensity and wavelength) in the absorbance spectra in the wavelength area A1 change due to the configurations of the cell masses 3, that is, the aggregation degrees of the cells in the cell masses 3, and the metabolites or the internal substances of the cells derived from the activities of the cells in the cell masses 3. In addition, changes in the absorbance spectra in the wavelength area A2 derive from the configurations of the cell masses 3, that is, the aggregation degrees of the cells in the cell masses 3. Therefore, by acquiring the distributions of the absorbances with respect to light in these wavelength areas A1 and A2, information related to the quality of the cell masses 3, that is, information related to the aggregation degrees and the activity degrees can be acquired.

Figure 4:
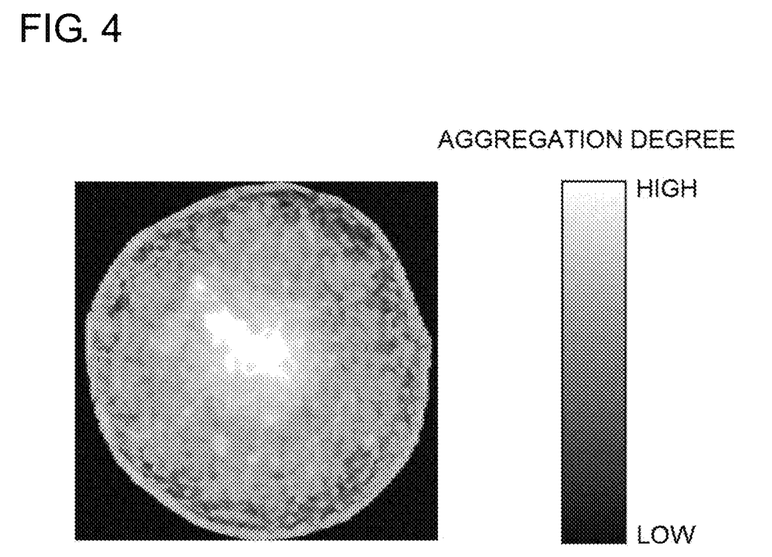
FIG. 4 is a diagram illustrating an evaluation of the aggregation degree of a cell mass.
Figure 5:
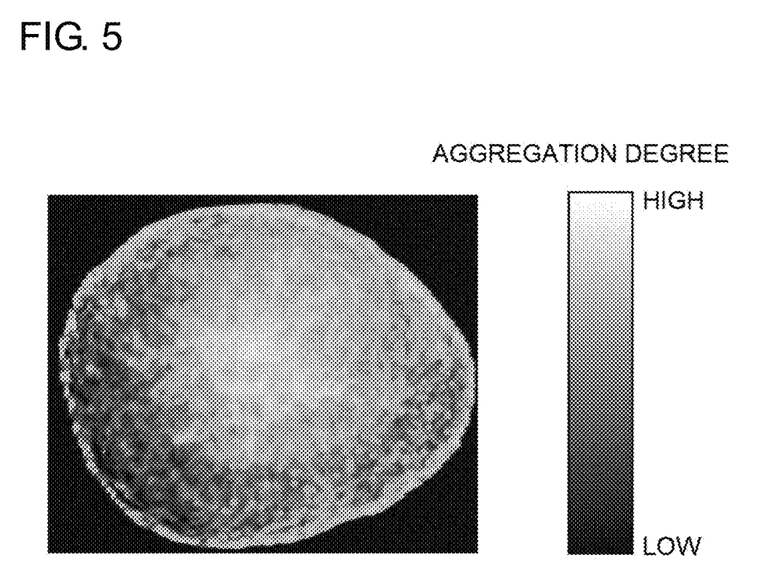
FIG. 5 is a diagram illustrating an evaluation of the aggregation degree of a cell mass.

FIG. 4 illustrates the results of evaluation of the aggregation degree of a cell mass A from information included in the absorbance spectrum. FIG. 5 illustrates the results of evaluation of the aggregation degree of a cell mass B from information included in the absorbance spectrum. Specifically, for each cell mass, from the transmitted light spectrum acquired as the light intensity distribution information by using the quality evaluation device 100, the absorbance spectrum is calculated for each pixel, and the absorbances with respect to light of a predetermined wavelength (wavelength of 1684 nm) in each wavelength area A2 are displayed for each pixel by a gray scale. It can be checked that, in the cell mass A, the aggregation degree of a central portion of the cell mass is high, whereas the aggregation degree of a peripheral portion of the cell mass is low. In addition, although, as in the cell mass A, it can be checked that, in the cell mass B, the aggregation degree of a central portion of the cell mass is high, whereas the aggregation degree of a peripheral portion of the cell mass is low, the aggregation degrees of both the central portion and the peripheral portion are lower in the cell mass B than in the cell mass A. That is, the aggregation degree of the cell mass B is lower than the aggregation degree of the cell mass A. Therefore, it is possible to conclude that the cell mass B matures more slowly than the cell mass A.

Figure 6:
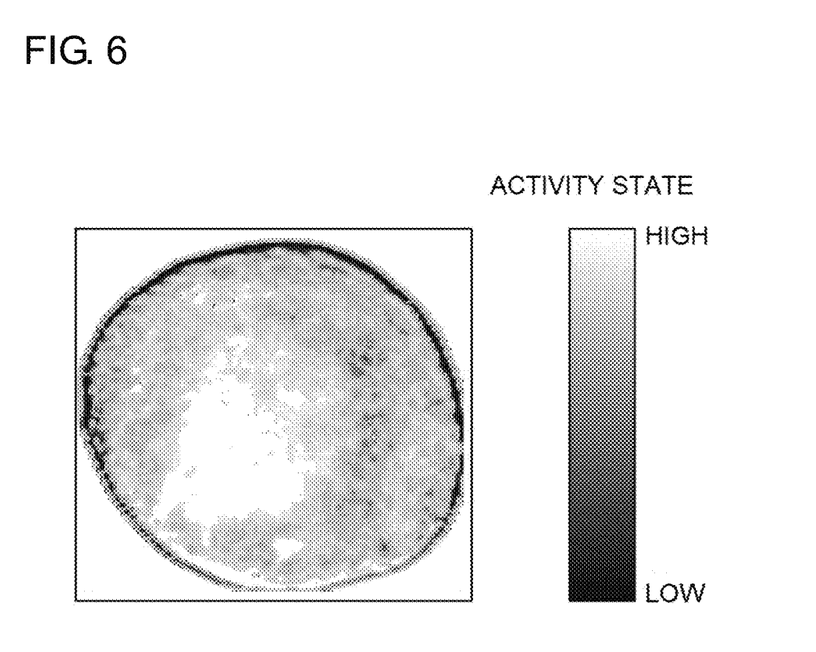
FIG. 6 is a diagram illustrating an evaluation of the activity state of a cell mass.
Figure 7:
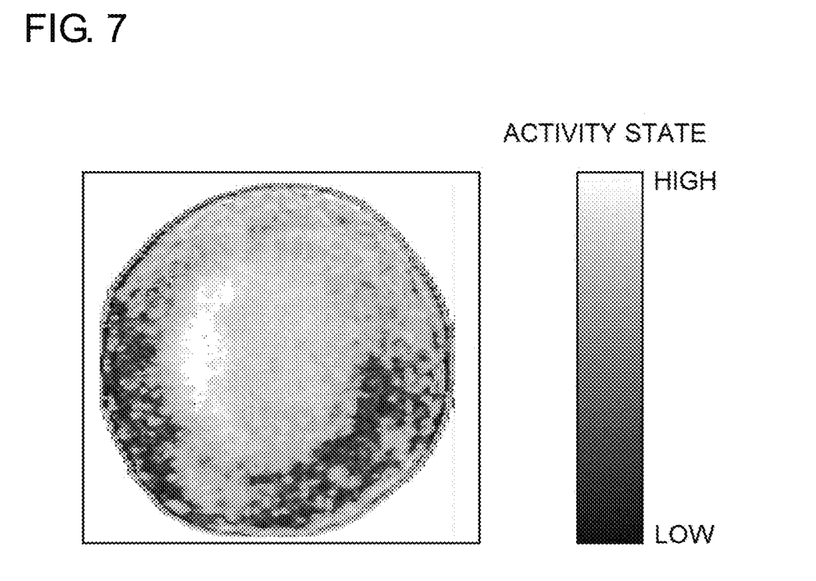
FIG. 7 is a diagram illustrating an evaluation of the activity state of a cell mass.

FIG. 6 illustrates the result of evaluation of the activity state (activity degree) of a cell mass C from information included in the absorbance spectrum. FIG. 7 illustrates the result of evaluation of the activity state (activity degree) of a cell mass D from information included in the absorbance spectrum. Specifically, for each cell mass, from the transmitted light spectrum acquired as the light intensity distribution information by using the quality evaluation device 100, the absorbance spectrum is calculated for each pixel, and the absorbances with respect to light of a predetermined wavelength (wavelength of 1615 nm) in each wavelength area A1 are normalized by using the absorbances with respect to light of a predetermined wavelength (wavelength of 1684 nm) in each wavelength area A2, after which the result is displayed for each pixel by a gray scale. It can be checked that, although, in the cell mass C, the activity state of a central portion of the cell mass is high and the activity state of a peripheral portion of the cell mass is lower than the activity state of the central portion, the activity state is high to a certain degree. In addition, it can be checked that, in the cell mass D, compared to the cell mass C, the activity state as a whole is low, in particular, the activity state in the peripheral portion thereof is low. That is, it is possible to conclude that the activity state of the cell mass D is lower than the activity state of the cell mass C, and that the activity degree of the cell mass D is lower than the activity degree of the cell mass C.

As described above, it is possible to evaluate the quality of a cell mass by using the light intensity distribution information in the cell mass.

It is to be noted that there are roughly two methods of evaluating the quality of a cell mass by using the light intensity distribution information related to the cell mass. The first method is, as shown in FIGS. 4 to 7, a method of evaluation after subjecting the light intensity distribution information to imaging. The second method is a method of evaluation without performing imaging.

In the first method, in the analyzing unit 30 of the quality evaluation device 100, information included in the light intensity distribution information and related to the absorbances corresponding to the positions in the cell masses is subjected to imaging to form images shown in, for example, FIGS. 4 to 7. Therefore, the quality is evaluated by using the images. It is possible to apply various methods to the evaluation of the quality by using the images. For example, it is possible to evaluate the quality by using, for example, the arrangement of colors in the images and use pattern recognition. As a pattern recognition method, a statistical discriminant analysis (for example, a principal component analysis, a regression analysis, a factor analysis) and machine learning (for example, a support vector machine (SVM), a kernel method, a Bayesian network method) that is a method in which data acquired in advance is experientially learned and newly acquired data is interpreted based on the learning result are available. However, the pattern recognition method is not limited thereto.

When these quality evaluation methods are used, a determination criterion is prepared with light intensity distribution information acquired from a cell mass whose quality is known being reference information. The above-described method is also applicable to a configuration in which the quality of a cell mass is evaluated in three or more ranks. In addition, images that are used in evaluating the quality of a cell mass can also be used when a user visually recognizes the state of the cell mass.

Although, in FIGS. 4 and 5, information related to the absorbance related to light of a particular wavelength is subjected to imaging after processing, such as normalization, as shown in FIGS. 6 and 7, it is possible to use information related to absorbances related to light of a plurality of wavelengths included in the absorbance spectra, and subject the information related to the absorbances corresponding to the positions in a cell mass to imaging. In this way, when the information included in the light intensity distribution information and related to the absorbances corresponding to the positions in a cell mass is to be subjected to imaging, it is not necessary to perform imaging by using all information included in the light intensity distribution information. In addition, it is possible add pretreatment, such as normalization, as appropriate.

In the second method, in the analyzing unit 30 of the quality evaluation device 100, numerical values included in the information that is included in the light intensity distribution information and that is related to the absorbances corresponding to the positions in a cell mass are used to evaluate the quality. Specifically, the numerical values included in the information related to the absorbances are measurement values of absorbances or numerical values acquired after, for example, average processing is performed as required. With a determination criterion such as, for example, whether or not numerical values corresponding to respective positions in a cell mass are included in a predetermined range being set in advance, the quality is evaluated based on this determination criterion. As a determination criterion, there exists, for example, a setting in which it is determined that the quality of a cell mass is in a good state when, of the numerical values that correspond to the respective positions in the cell mass included in the light intensity distribution information related to the same cell mass, the number of numerical values included in a predetermined range exceeds a predetermined value. However, the determination criterion is not limited thereto. In addition, when the quality is to be evaluated in three or more ranks, a determination criterion may be set for each rank in advance. Further, it is possible to add pretreatment, such as normalization, as appropriate.

When, as in the second method, there is used a configuration in which the numerical values included in the information that is included in the light intensity distribution information and that is related to the absorbances corresponding to the positions in the cell mass are used to evaluate the quality, it is possible to evaluate the quality of the cell mass in a non-destructive manner without performing processing, such as imaging. Therefore, it can be said that it is possible to more easily evaluate the quality of the cell mass.

There may be used a configuration in which an overall determination is performed by combining the evaluation results obtained by the first method and the evaluation results obtained by the second method. Since various quality evaluation methods can be considered as described above, it is possible to combine such methods.

Although, in the above embodiment, a configuration that uses the light intensity distribution information when evaluating the quality of a cell mass has been described, in addition to the above-described methods, a configuration may be used in which a transmission spectrum of a cell mass is acquired at every elapsed time (for example, about 36 to 48 hours at every 6 to 10 hours), and the quality of the cell mass is evaluated based on a change in the light intensity distribution information over time. In this case, since it is possible to check a change in the cell mass over time from the light intensity distribution information, it is possible to evaluate the quality with accuracy. In this way, since there are various methods of evaluating the quality based on the transmission spectrum of the cell mass, a method can be selected as appropriate according to, for example, the type and state of a cell mass to be evaluated.

In this way, according to the quality evaluation method and the quality evaluation device according to the present invention, by using a configuration in which quality evaluation is performed based on the light intensity distribution information acquired by irradiating a cell mass with measurement light including near-infrared light, it is possible to evaluate the quality of the cell mass in a non-destructive/non-invasive manner. By using near-infrared light, it is possible to acquire information of the inside of a cell mass and information related to absorbance distribution thereof, so that, by using information related to cells corresponding to positions in the cell mass, it is possible to acquire more detailed information related to the quality of the cell mass. Therefore, it is possible to perform quality evaluation with high accuracy.

It is to be noted that it is possible to even change as appropriate the light source 10 and the detection unit 20 for acquiring the light intensity distribution information related to a cell mass. For example, a configuration that does not include spectroscopic means may be used. It is possible to, as the light source 10, prepare a plurality of laser diodes (LDs) that are capable of emitting light of a particular wavelength and to change the wavelength of measurement light that is emitted from the light source 10 by switching the LD that emits the measurement light. When, in this way, the light that is emitted from the light source 10 is controlled, it is possible to acquire information related to absorbance with respect to light of a particular wavelength even if the detection unit 20 does not include spectroscopic means. In addition, by configuring the light source 10 by combining a light emitting diode (LED) and a plurality of bandpass filters instead of using the above-described plurality of LDs, it is possible to change the wavelength of measurement light that is emitted from the light source 10.

In addition, although, in the above-described embodiment, in the quality evaluation device 100, a configuration is described in which a plane spectroscopic operation is performed to allocate positional information of a measurement object to pixels arranged in a first direction among a plurality of pixels that are two-dimensionally arranged, and to allocate wavelength information to pixels arranged in a second direction to acquire a hyperspectral image, a configuration in which light intensity distribution information for each wavelength is repeatedly acquired may be used.

The invention claimed is:

1. A quality evaluation method comprising:
an acquisition step of, by irradiating a cell mass with measurement light including near-infrared light, acquiring light intensity distribution information including information related to a distribution of absorbance with respect to the measurement light in the cell mass; and
an evaluation step of evaluating a quality of the cell mass based on the light intensity distribution information from a plurality of positions in the same cell mass, wherein
the quality of the cell mass comprises an aggregation degree and an activity degree of the cell mass.

2. The quality evaluation method according to claim 1, wherein the evaluation step comprises imaging light intensity information that is included in the light intensity distribution information and that corresponds to positions in the cell mass.

3. The quality evaluation method according to claim 1, wherein the evaluation step comprises evaluating the quality by using numerical values included in light intensity information that is included in the light intensity distribution information and that corresponds to positions in the cell mass.

4. A quality evaluation device comprising:
a light source that irradiates a cell mass with measurement light including near-infrared light;
a light receiving unit including a receiving surface that, by receiving transmitted light or diffusely reflected light from the cell mass, acquires light intensity distribution information including information related to a distribution of absorbance with respect to the measurement light in the cell mass, the transmitted light or the diffusely reflected light being emitted from the cell mass by irradiating the cell mass with the measurement light; and
an analyzing unit including a computer that evaluates a quality of the cell mass based on the light intensity distribution information from a plurality of positions in the same cell mass, wherein
the quality of the cell mass comprises an aggregation degree and an activity degree of the cell mass.

* * * * *